United States Patent [19]

Rieber et al.

[11] Patent Number: 4,491,674

[45] Date of Patent: Jan. 1, 1985

[54] PROCESS AND APPARATUS FOR THE SAFE SUPPLY OF MOLECULAR OXYGEN OR OF GAS CONTAINING MOLECULAR OXYGEN TO AN OXIDATION OF HYDROCARBONS

[75] Inventors: Norbert Rieber, Mannheim; Hans Hellbach, Lampertheim; Gerhard Hunziker; Guenter Mueller, both of Ludwigshafen, all of Fed. Rep. of Germany

[73] Assignee: BASF Aktiengesellschaft, Fed. Rep. of Germany

[21] Appl. No.: 213,793

[22] Filed: Dec. 8, 1980

[30] Foreign Application Priority Data

Jan. 19, 1980 [DE] Fed. Rep. of Germany ....... 3001880

[51] Int. Cl.$^3$ .............................................. C07C 45/33
[52] U.S. Cl. .................... 568/357; 423/579; 568/570; 568/836; 549/532
[58] Field of Search ............... 568/357, 358, 836, 950, 568/954, 320

[56] References Cited

U.S. PATENT DOCUMENTS 2,009,663 7/1935 James .................................. 568/950
3,006,944 10/1961 Fenske et al. ........................ 568/950
3,170,863 2/1965 Spillane et al. ...................... 568/950

FOREIGN PATENT DOCUMENTS 2452803 5/1976 Fed. Rep. of Germany ...... 568/357
510599 9/1971 Switzerland ........................ 568/357

*Primary Examiner*—James H. Reamer
*Attorney, Agent, or Firm*—Keil & Weinkauf

[57] ABSTRACT

A process for the safe supply of molecular oxygen or gas containing molecular oxygen to an oxidation of hydrocarbons in the liquid phase, wherein, immediately before the point of entry into the liquid hydrocarbon, the oxygen, or gas containing oxygen, to be supplied is at least 20° C. colder than the hydrocarbon, and wherein, as soon as the oxygen, or gas containing oxygen, which is to be supplied exceeds the predetermined temperature at the supply orifice, the supply ceases.

2 Claims, 2 Drawing Figures

PROCESS AND APPARATUS FOR THE SAFE SUPPLY OF MOLECULAR OXYGEN OR OF GAS CONTAINING MOLECULAR OXYGEN TO AN OXIDATION OF HYDROCARBONS

The oxidation of, for example, cyclohexane, with molecular oxygen, in the liquid phase, is carried out industrially in order to produce cyclohexanol (cf. Swiss Pat. No. 510,599). The molecular oxygen is supplied to the reaction zone via, for example, two-material nozzles, dip tubes, frits or similar devices. In carrying out such a process, it must be borne in mind that oxygen forms explosive mixtures with hydrocarbons. Penetration of the hydrocarbon to be oxidized into the supply line of the oxygen or oxygen-containing gas is particularly dangerous. Equally, the formation of a submerged flame constitutes a danger, since it can cause the supply device to melt.

Examples of devices which are employed in order to prevent penetration of hydrocarbons into the lines in which oxygen is present include instruments which respond to pressure difference or to flow rate and which, when these parameters fall below a certain minimum, interrupt the supply of oxygen, and hence interrupt the reaction, by flushing the lines with nitrogen. However, such methods are prone to faults and have the disadvantage that the points of measurement of the pressure difference or of the flow rate can only be located outside the reaction chamber, so that if there is a sudden leak in the lines between the points of measurement and the reaction chamber the pressure difference or flow rate does not drop and hence the supply of oxygen is not interrupted.

According to German Laid-Open Application DOS No. 2,452,803, a thermocouple is located at the point at which the molecular oxygen leaves the line and enters the reaction medium, so as to monitor the temperature and to interrupt the oxygen supply if a submerged flame is formed. This procedure has not proved successful for detecting the penetration of hydrocarbons into the oxygen-containing line in good time, before an explosion occurs or a submerged flame develops. If oxygen is supplied through a dip tube, the molecular oxygen heats up on the hot walls, until it virtually reaches the reaction temperature. Accordingly, the temperature indicated by the thermocouple is virtually identical with the reactor temperature, and penetration of hydrocarbon into the oxygen-containing line thus does not immediately manifest itself clearly through a temperature rise. This is very particularly true when molecular oxygen is introduced through the outer annular gap of a two-material nozzle whilst preheated hydrocarbons are simultaneously introduced through the inner bore. In that case, the molecular oxygen is heated up both by the outer part and the inner part of the two-material nozzle.

It is an object of the present invention to provide a process and apparatus which make it possible to supply molecular oxygen, or gas containing molecular oxygen, to the oxidation of hydrocarbons in the liquid phase in such a way that if hydrocarbons penetrate into the oxygen-containing lines, or if a submerged flame is formed, the oxidation is interrupted in good time.

We have found that this object is achieved by a process for the safe supply of molecular oxygen or gas containing molecular oxygen to the oxidation of hydrocarbons in the liquid phase, wherein the molecular oxygen, or gas containing molecular oxygen, which is to be supplied is, immediately before the point of entry into the liquid hydrocarbon being oxidized, at least 20° C. colder than the hydrocarbon, and wherein, as soon as the molecular oxygen, or gas containing molecular oxygen, which is to be supplied exceeds the predetermined temperature at the supply point, the supply ceases.

The invention further relates to apparatus for introducing molecular oxygen, or gas containing molecular oxygen, into liquid hydrocarbons, which comprises a tubular jacket 1 with an exit nozzle 2 and a supply tube 4 for molecular oxygen, or gas containing molecular oxygen, which is located lengthwise in the jacket and is kept at a distance therefrom by spacers 3, and wherein the supply tube 4 terminates within the jacket 1 before the exit nozzle 2, and a temperature-measuring element 5 is located between the end of the supply tube 4 and of the exit nozzle 2.

The novel process and the novel apparatus have the advantage that the penetration of hydrocarbons into the oxygen-containing supply lines is reliably detectable and the formation of a submerged flame is avoided.

The process according to the invention may be used, for example, in the liquid phase oxidation of cycloalkanes to cycloalkyl hydroperoxides or to cycloalkanols and cycloalkanones, and for the direct oxidation of propylene to propylene oxide, as well as for the cooxidation of hydrocarbons, for example the preparation of propylene oxide by co-oxidation of propylene and ethylbenzene. The process according to the invention has acquired particular industrial importance for the oxidation of cyclohexane, described, for example, in Swiss Pat. No. 510,599. As a rule, the oxidation of cyclohexane is carried out by introducing molecular oxygen, or gas containing molecular oxygen, into the liquid reaction mixture at from 140° to 200° C. under a pressure of from 10 to 60 bar, in the presence or absence of a catalyst, such as a cobalt salt.

According to the invention, the procedure followed is such that the molecular oxygen, or gas containing molecular oxygen, which is supplied is, immediately before the point of entry into the hot liquid hydrocarbon, i.e. at the nozzle orifice, at least 20° colder than the hydrocarbon. If, for example, cyclohexane is being oxidized at 180° C., the molecular oxygen supplied should not be at above 160° C. shortly before the nozzle orifice. An advantageous manner of achieving this, in the case of molecular oxygen supply lines which protrude into the hot reaction mixture, is to prevent or reduce heat transfer from the hot reaction mixture to the molecular oxygen to be supplied. It has proved particularly advantageous to surround the molecular oxygen supply line, protruding into the hot reaction mixture, by an insulating layer of gas. A simple manner of achieving this is to surround the supply line by a further wider tube, which can have a somewhat constricted exit end, with the proviso that the molecular oxygen supply line terminates before the surrounding tube. As a result, an insulating layer of gas is formed when oxygen is being supplied. The temperature of the molecular oxygen is measured in the space between the exit of the molecular oxygen from the supply line and the orifice of the jacket. As soon as the oxygen exceeds the maximum allowed temperature at its exit orifice, the supply of molecular oxygen or of gas containing molecular oxygen is interrupted. In that event, it is advantageous immediately to flush the supply line automatically with nitrogen or some other inert gas. This ensures that no uncontrolled reaction occurs in the molecular oxygen supply line, and that a submerged flame is not formed. The temperature of the molecular oxygen at the exit point can also be advantageously influenced by appropriate choice of the crosssection of the supply line and of the flow velocity of the molecular oxygen. Suitable values for these parameters can easily be established by simple preliminary experiments.

Figure 1:
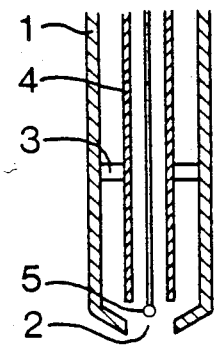
FIGS. 1 to 3 are embodiments of the novel apparatus.

An example of a suitable apparatus for carrying out the process is shown in FIG. 1. The apparatus comprises a tubular jacket 1 with an exit nozzle 2, which is advantageously constricted, for the gas to be introduced. A supply tube 4 for molecular oxygen or gas containing molecular oxygen is located lengthwise within the jacket, and is kept at a distance from the latter by spacers 3. The supply tube 4 terminates within the jacket 1 before the exit nozzle 2. As a result, when oxygen is passed through the tube 4 the space between this tube and the jacket 1 is automatically filled with oxygen, and an insulating layer of gas is formed. A temperature-measuring element 5 is located between the end of the supply tube 4 and of the exit nozzle 2. An example of a suitable element is a Ni/CrNi thermocouple. Advantageously, the element 5 used for temperature measurement is led through the supply tube 4 so as to minimize the effect of the hot reaction medium on the element.

Figure 2:
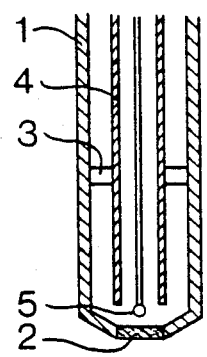

Another embodiment is shown in FIG. 2, where 1 is a tubular jacket, 2 is an exit nozzle provided with a frit, 3 is a spacer, 4 is a supply tube and 5 an element for temperature measurement. Instead of a frit, a plurality of nozzles could be used.

Figure 3:
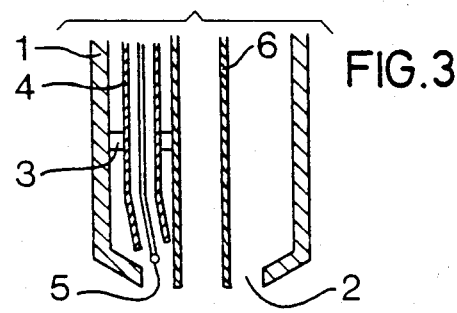

The two-material nozzle in FIG. 3 constitutes yet a further embodiment. Here, 1 is a tubular jacket, 2 an exit orifice for the materials to be introduced into the reaction mixture, 3 is a spacer, 4 is a supply tube for molecular oxygen or gas containing molecular oxygen, 5 is an element for temperature measurement and 6 is a supply tube for hydrocarbons.

We claim:

1. In a process for producing cyclohexanol and cyclohexanone or cyclohexyl hydroperoxide by oxidizing liquid cyclohexane at a temperature of from about 140° to 200° C. and at a pressure of from 10 to 60 bar, the improvement which comprises: passing molecular oxygen or a gas containing molecular oxygen through a tube and into the liquid cyclohexane, said molecular oxygen or gas containing molecular oxygen having a temperature immediately before contact with the liquid cyclohexane which is at least 20° C. lower than the temperature of the cyclohexane, said tube through which said oxygen or gas containing oxygen is passed being surrounded at least at the exit opeining of the tube by a layer of insulating gas of molecular oxygen or a gas containing molecular oxygen; and interrupting the supply of oxygen or gas containing oxygen through the tube as soon as the temperature of the oxygen or oxygen containing gas is less than 20° C. lower than the temperature of the liquid cyclohexane.

2. The process of claim 1, wherein the molecular oxygen, or gas containing molecular oxygen, which is to be supplied is from 20° to 150° C. colder than the hydrocarbon.

* * * * *